United States Patent [19]

Knoll et al.

[11] 4,291,036
[45] Sep. 22, 1981

[54] PYRIDO[1,2-A]PYRIMIDINE DERIVATIVES AND METHOD OF ANALGESIC TREATMENT

[75] Inventors: Jozsef Knoll; Zoltan Meszaros; Istvan Hermecz, all of Budapest; Ferenc Fülöp; Gabor Bernath, both of Szeged; Sandor Virag, Budapest; Gabor Nagy, Budapest; Peter Szentmiklosi, Budapest, all of Hungary

[73] Assignee: Chinoin Gyogyszer es Vegyeszeti Termekek Gyara Rt., Budapest, Hungary

[21] Appl. No.: 130,371

[22] Filed: Mar. 14, 1980

Related U.S. Application Data

[63] Continuation-in-part of Ser. No. 934,801, Aug. 17, 1978, Pat. No. 4,219,649.

[30] Foreign Application Priority Data

Aug. 19, 1977 [HU] Hungary .............................. CI 1765

[51] Int. Cl.³ .................. A61K 31/505; C07D 487/04
[52] U.S. Cl. .................................... 424/251; 544/282
[58] Field of Search ........................ 544/282; 424/251

[56] References Cited

U.S. PATENT DOCUMENTS

| | | | |
|---|---|---|---|
| 3,585,198 | 6/1971 | Meszaros et al. | 544/282 |
| 3,898,224 | 8/1975 | Yale et al. | 544/282 |
| 4,022,897 | 5/1977 | Yale et al. | 424/251 |
| 4,209,622 | 6/1980 | Meszaros et al. | 544/282 |

FOREIGN PATENT DOCUMENTS 1492573 11/1977 United Kingdom ................ 544/282

OTHER PUBLICATIONS

Yale et al., Chemical Abstracts, vol. 86, 29741d (01/31/77).
Shur et al., Chemical Abstracts, vol. 69, 52090y (1968).
Brown et al., Chemical Abstracts, vol. 75, 48839f (1971).

Primary Examiner—Donald G. Daus
Assistant Examiner—Diana G. Rivers
Attorney, Agent, or Firm—Karl F. Ross

[57] ABSTRACT

Compounds of the formula

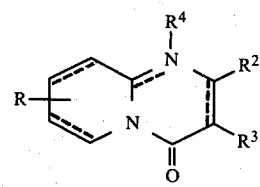

or pharmaceutically acceptable acid-addition or quaternart ammonium salts thereof
wherein
R is hydroxy, carboxy, lower alkoxycarbonyl, benzyloxycarbonyl, phenoxycarbonyl, carbamoyl, N-loweralkyl-carbamoyl, N,N-dilower-alkyl-carbamoyl, carboazido, carbohydrazido or cyano;
$R^2$ is $C_1$ to $C_6$ alkyl;
$R^3$ is $C_1$ to $C_6$ alkyl or benzyl; and
$R^4$ is a single electron pair, hydrogen or lower alkyl; and the dotted lines represent saturated or unsaturated bonds, are disclosed with analgesic properties.

4 Claims, No Drawings

PYRIDO[1,2-A]PYRIMIDINE DERIVATIVES AND METHOD OF ANALGESIC TREATMENT

CROSS REFERENCE TO RELATED APPLICATIONS

This application is a continuation-in-part of copending application Ser. No. 934,801 filed Aug. 17, 1978, U.S. Pat. No. 4,219,649, the contents of which are expressly incorporated herein.

FIELD OF THE INVENTION

This invention relates to pyrido[1,2-a]pyrimidine derivatives, a process for the preparation thereof and pharmaceutical compositions containing the same.

DESCRIPTION OF THE INVENTION

The present invention is directed more particularly to 2-alkyl-3-substituted-4-oxo-4H-pyrido[1,2-a]pyrimidines. The great majority of the compounds of the present invention are new, never described in the prior art.

There are, however, a few publications dealing with 2-alkyl-3-substituted-4-oxo-4H-pyrido[1,2-a]pyrimidines. It is known that 2-aminopyridine and ethyl-2-methyl-acetoacetate or ethyl-2-ethyl-acetoacetate may be reacted in a molar ratio of 1:1.5 in polyphosphoric acid at 100° C.; on neutralizing the reaction mixture the corresponding pyrido[1,2-a]pyrimidines are obtained (J. Org. Chem. 33, 3015 (1968). According to another method 2-aminopyridine and ethyl-2-methyl-acetoacetate are reacted at 165° C. in the presence of polyphosphoric acid ethyl ester, the reaction mixture is poured on to ice cold water and neutralized with ammonia. After column-chromatographic purification 2,3-dimethyl-4-oxo-4H-pyrido[1,2-a]pyrimidine is obtained with a yield of 42%; mp.: 119.5°–121° C. (J. Chem. Soc. C. 1970, 829 and J. Chem. Soc. C. 1971, 2163). In these publications the 2,3-dimethyl-, 2-methyl-3-ethyl-, 2,3,7-trimethyl-, 2-methyl-3-ethyl-7-bromo- and 2,6,8-trimethyl-3-ethyl-4-oxo-4H-pyrido[1,2-a]pyrimidine are described without disclosure of any therapeutical utility of these compounds.

According to a feature of the present invention there are provided new pyrido[1,2-a]pyrimidine derivatives of the formula:

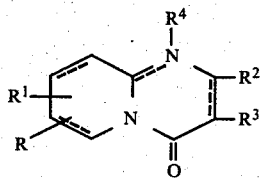

and salts and quaternary salts thereof
(wherein
R is hydrogen, halogen, lower alkyl, nitro, hydroxy, amino, lower alkoxy, carboxy or a derivative of the carboxy group;
$R^1$ is hydrogen, halogen or lower alkyl;
$R^2$ is an alkyl group having 1 to 16 carbon atoms;
$R^3$ is an alkyl group having 1 to 16 carbon atoms, a $C_{7-12}$ aralkyl group optionally halogeno-substituted in the aromatic ring; or a cycloalkyl-alkyl group having 6 to 12 carbon atoms; and
$R^4$ is a single electron pair, a hydrogen atom or a lower alkyl group;
the dotted lines represent optional bonds;

With the proviso that if all the dotted lines are further bonds, $R^2$ and $R^3$ are methyl and $R^1$ is hydrogen, then R is other than hydrogen or 7-methyl; and with the further proviso that if all the dotted lines are further bonds, $R^2$ is methyl, $R^3$ is ethyl and $R^1$ is hydrogen, then R is other than hydrogen or 7-bromo and with the further proviso that if all the dotted lines are further bonds, $R^2$ is methyl, $R^3$ is ethyl and $R^1$ is 6-methyl, then R is other than 8-methyl).

The term "lower alkyl" used throught the specification identifies straight or branched chain alkyl groups having 1 to 6, preferably 1 to 4 carbon atoms (e.g. methyl, ethyl, n-propyl, isopropyl, N-butyl etc.). The term "lower alkoxy" means straight or branched chain alkoxy groups having 1 to 6, preferably to 1 to 4 carbon atoms (e.g. methoxy, ethoxy, n-propoxy, isopropoxy etc.). The term "halogen" encompasses the fluorine, chlorine, bromine and iodine atoms. If $R^2$ or $R^3$ stand for $C_{1-16}$ alkyl groups they can represent methyl, ethyl, n-propyl, isopropyl, n-butyl, n-pentyl, n-hexyl, n-decyl, n-dodecyl groups etc. The term "derivative of the carboxy group" relates to esters (e.g. alkyl, aryl, preferably phenyl, or aralkyl preferably benzyl esters), acid amides (e.g. carbamoyl, N-alkyl- or N,N-dialkyl-carbamoyl groups etc.), acid azides, acid hydrazides or nitriles. The said acid derivatives can be preferably lower alkyl esters (alkoxycarbonyl). The term "$C_{7-12}$ aralkyl" may be preferably benzyl, beta-phenyl-ethyl, gamma-phenyl-propyl etc. The $C_{6-12}$ cyclo alkyl-alkyl group can be preferably cyclohexyl-methyl, cyclopentyl-methyl, cyclohexyl-ethyl etc.

The salts of the compounds of the formula I can be pharmaceutically acceptable salts formed with organic or inorganic acids (e.g. hydrochlorides, hydrobromides, hydroiodides, sulfates, phosphates, maleates, tartarates, acetates, lactates, fumarates etc). The quaternary salts may be formed with conventional quaternarizing agents (e.g. with alkyl halides or dialkyl sulfates such as methoiodides, methobromides, methochlorides, methosulfates, ethoiodides etc.).

In a preferred group of the compounds of formula I, $R^2$ is $C_{1-6}$ alkyl, $R^3$ is $C_{1-6}$ alkyl; R is 6-methyl and $R^1$ is hydrogen. Those compounds are particularly preferred when the bonds marked by a dotted line are not hydrogenated.

A particularly advantageous group consists of those compounds of the formula I in which R is hydrogen, chlorine, methyl, nitro, hydroxy, carboxy or lower alkoxycarbonyl; $R^1$ is hydrogen or methyl; $R^2$ is methyl, ethyl, n-propyl or isopropyl; $R^3$ is methyl, ethyl, n-propyl, isopropyl, n-butyl, n-dodecyl, benzyl, p-chlorobenzyl or cyclohexylmethyl; $R^4$ stands for a single electron pair, hydrogen or methyl; and the dotted lines represent optional further bonds with the provisos enumerated before.

Particularly preferred representatives of the compounds of the formula I are the following derivatives:
2,3,6-trimethyl-4-oxo-4H-pyrido[1,2-a]pyrimidine and its acid addition salts and quaternary salts;
3,6-dimethyl-2-ethyl-4-oxo-4H-pyrido[1,2-a]pyrimidine and its acid addition salts and quaternary salts;
2-methyl-3-n-propyl-4-oxo-4H-pyrido[1,2-a]pyrimidine and its acid addition salts and quaternary salts;
2,6-dimethyl-3-n-propyl-4-oxo-4H-pyrido[1,2-a]pyrimidine and its acid addition salts and quaternary salts;

2,9-dimethyl-3-ethyl-4-oxo-4H-pyrido[1,2-a]pyrimidine and its acid addition salts and quaternary salts;

2,9-dimethyl-3-ethyl-4-Oxo-4H-pyrido[1,2-a]pyrimidine and its acid addition salts and quaternary salts;

2,7-dimethyl-3-ethyl-4-oxo-4H-pyrido[1,2-a]pyrimidine and its acid addition salts and quaternary salts;

2,8-dimethyl-3-ethyl-4-oxo-4H-pyrido[1,2-a]pyrimidine and its acid addition salts and quaternary salts;

2-methyl-3-ethyl-7-chloro-4-oxo-4H-pyrido[1,2-a]pyrimidine and acid addition salts and quaternary salts thereof; and 2,6-dimethyl-3-n-butyl-4-oxo-4H-pyrido[1,2-a]pyrimidine and acid addition salts and quaternary salts thereof.

A highly active compound of the formula I is the 2,6-dimethyl-3-ethyl-4-oxo-4H-pyrido[1,2-a]pyrimidine and salts and quaternary salts—especially the hydrochloride—thereof.

Another particularly advantageous group of compounds contemplated by the invention include compounds of the formula Ia:

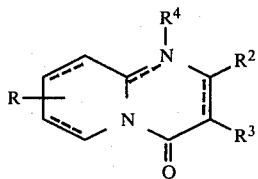

or pharmaceutically acceptable acid addition or quaternary ammonium salts thereof wherein R is hydroxy, carboxy, loweralkoxycarbonyl, benzyloxycarbonyl, phenoxycarbonyl, carbamoyl, N-loweralkyl-carbamoyl, N,N-diloweralkylcarbamoyl, carboazido, carbohydrazido or cyano;

$R^2$ is $C_1$ to $C_6$ alkyl;

$R^3$ is $C_1$ to $C_6$ alkyl or benzyl; and $R^4$ is a single electron pair, hydrogen or lower alkyl; and the dotted lines represent saturated or unsaturated bonds. A particularly preferred group of compounds involves those compounds mentioned immediately above where R is 9-hydroxy or is 6-, 7-, or 8-carboxy, loweralkoxycarbonyl, benzyloxycarbonyl, phenoxycarbonyl, carbamoyl, N-loweralkylcarbamoyl, N,N-diloweralkylcarbamoyl, carboazido, carbohydrazido or cyano.

Particularly preferred representatives of the compounds of formula Ia include:

2-methyl-3-ethyl-9-hydroxy-4-oxo-4H-pyrido[1,2-a]pyrimidine;

2-methyl-3-benzyl-9-hydroxy-4-oxo-4H-pyrido[1,2-a]pyrimidine;

2-methyl-3-ethyl-9-carboxyl-4-oxo-4H-pyrido[1,2-]pyrimidine; and 2-methyl-3-ethyl-8-ethoxycarbonyl-4-oxo-4H-pyrido[1,2-a]pyrimidine;

or pharmaceutically acceptable acid addition or quaternary ammonium salts thereof.

It is known that 1,6-dimethyl-3-ethoxycarbonyl-4-oxo-4H-6,7,8,9-tetrahydro-pyrido[1,2-a]pyrimidinium-methosulfate (referred to below as Probon, British Pat. No. 1,209,947) is an outstanding analgesic of the pyrido[1,2-a]pyrimidine group. The analgesic effects is only one of the manifestations of its central effects which is utilized in therapy. The sedative effect of its higher doses could be demonstrated in various behavior tests. Doses as high as 250 mg./kg., or above, when injected s.c. caused inhibition of the conditioned reflex in the respective tests and elicited characteristic desynchronization of the EEG (Knoll et al.: Arzenimittelforschung 21, 727-732 (1971). All these central effects appeared upon adminstration of relatively high doses. In man too analgesic doses are likely to produce other CNS side effects which, however, do not involve significant problems.

Beagles are much more sensitive to CNS effects than rats, Rhesus monkeys and man. Therefore, relatively low doses of Probon are found to cause disturbances of coordination and behavior, as well as atazia. In the case of oral administration, these effects appear at doses of above 100 mg./kg. body weight, at the 150-200 mg./kg. dose level these symptoms are very marked, and 300 mg./kg. the death of the animal.

The analgesics cspectrum of Probon significantly differs from that of the major analgesics acting on the opiate receptors (Knoll, J.: Syposium on analgesics pp 3-18, Academic Press, Budapest 1976, Eds.: J. Knoll and E. S. Vizi). This unique behavior implies the presence of pyridopyrimidine sensitive receptors in the central nervous system, through which these structures exert inter alia their analgesic effect.

Based on the above assumption, structure-activity studies have been carried out with the aim to improve the activity spectrum of this series of compounds. It has been found that the new compounds of the formula I are capable of meeting these requirements. An outstanding member of this group is the 2,6-dimethyl-3-ethyl-4-oxo-4H-pyrido[1,2-a]pyrimidine and salts and quaternary salts thereof, particularly in free base form and as the hydrochloride. This compound group and particularly the abovementioned derivative was found to be a more potent analgesic than Probon in both rat and dog, while even in high doses failing to elicit the CNS symptoms observed with high doses of Probon in rats and with its low doses in dogs. This appears to support our hypothesis of a selective pyrido[1,2-a]pyrimidine-sensitive receptor in the CNS. The fact that the compounds of the formula I—particularly 2,6-dimethyl-3-ethyl-4-oxo-4H-pyrido-[1,2-a]pyrimidine—strongly inhibit the CNS effects of Probon proves the strong affinity of this compound group to these receptors without possessing specific activity of its own. The lack of toxicity of the compounds of the formula I in Beagles is considered as a further proof of this hypothesis. Doses as high as 1 g./kg. do not cause toxic changes or death of the animals, but in a dose as low as 50 mg./kg. it antagonizes the effect of twice the lethal dose (600 mg./kg.) of Probon. Dogs treated this way showed complete analgesia, without the slightest sign of incoordination or ataxia, and no death occurred.

The above facts prove that the compounds of the formula I are new pyrido[1,2-a]pyrimidine derivatives with an activity spectrum substantially differing from that of Probon. It is significantly superior to Probon in the therapeutic aspect as well as its higher analgesic potency; it is devoid of CNS side effects.

According to a further feature of the present invention there is provided a process for the preparation of compounds of the formula I and salts and quaternary salts thereof (wherein the substituents have the same meanings as stated before except the proviso which comprises reacting a 2-amino-pyridine of the formula II

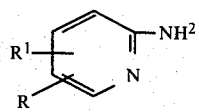

or an acid addition salt thereof (wherein R and R¹ have the same meaning as stated above) with a beta-oxo-ester of the formula III

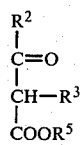

(wherein R² and R³ have the same meaning as stated above and R⁵ is lower alkyl)—whereby in the case of the preparation of 2,3-dimethyl-, 2-methyl-3-ethyl-, 2,3,7-trimethyl-, 2-methyl-3-ethyl-7-bromo- and 2,6,8-trimethyl-3-ethyl-4-oxo-4H-pyrido[1,2-a]pyrimidine, the reaction is carried out in the mixture of phosphorous oxychloride and polyphosphoric acid—and thereafter, if desired, reducing the compound of the formula IV thus obtained

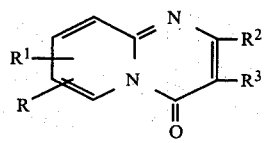

(wherein R¹, R², R³ and R are as stated above) and if desired, converting a compound of the formula I into another compound of the formula I by methods known per se, if desired, converting a halogenoalkyl substituent into an alkyl substituent by methods known per se and, if desired, converting a compound of the formula I into its salt or quaternary salt or setting it free from its salt or transforming a salt into another salt.

The reaction between the compounds of the formulae II and III is carried out preferably in the presence of an acidic condensing agent. For this purpose phosphoric acid and derivatives thereof, hydrogen halides, p-toluene-sulfonic acid, concentrated sulfuric acid, alkanoic acids, alkanoic acid anhydrides or mixtures thereof can be used. The phosphoric acid derivatives can be orthophosphoric acid, polyphosphoric acid or lower alkyl esters thereof. The reaction may be carried out in the presence or in the absence of a solvent. One may proceed preferably by using phosphorous oxychloride as solvent and a catalytic amount of polyphosphoric acid or a derivative thereof as acidic condensing agent. Thus the desired compounds are obtained in particularly pure form and with high yields.

The reaction mixture may be decomposed by the addition of a lower alkanol (such as methanol or ethanol). Thus a compound of the formula IV (wherein R¹, R², R³ and R have the same meaning as stated above) is obtained as the hydrochloride thereof. This derivative precipitates in crystalline form and can be easily isolated.

According to a preferred embodiment of the process, 0.5 to 1.5 moles of a compound of the formula II and 0.5–1.5 moles of a compound of the formula III are reacted in the presence of 0.5–10.0 moles, preferably 2–5 moles of phosphorous oxychloride and 1–150 g. of polyphosphoric acid (the two latter components are related to 1 mole of a compound of the formula II). Cyclization is carried out at 20°–200° C., preferably at 80°–160° C.

If the reaction mixture is decomposed with water or an alkali, the compound of the formula IV is obtained in the form of the free base.

One may also proceed by reacting the compounds of the formulae II and III in a 2–15-fold amount of polyphosphoric acid. Thus 1 mole of 2-amino-pyridine of the formula II is preferably reacted with 0.5–1.5 moles of a compound of the formula III. The reaction is carried out at 40°–200° C., preferably at a temperature of 60° to 180° C.

The reaction time depends on the temperature and the reactants and is generally 0.1 to 10 hours. The reaction mixture may be worked up by conventional methods, e.g. by diluting the reaction mixture with water, neutralizing it with alkali and precipitating the compound of the formula IV as the free base. In this embodiment of the process a solvent, preferably chlorinated hydrocarbons (e.g. chloroform, chlorobenzene etc.), may be used.

If a hydrogen halide is used as acidic condensing agent one may proceed, preferably, by pre-forming the hydrohalide salt of the compound of the formula II and reacting the said salt with the compound of the formula III in the presence of an aromatic tertiary nitrogen compound as solvent.

As hydrogen halide one may use hydrogen chloride, hydrogen bromide or hydrogen iodide; the aromatic tertiary nitrogen containing solvent may be pyridine, picoline, lutidine, quinoline etc. The compound of the formula III may be preferably used in an amount of 0.5–1.5 moles related to 1 mole of a compound of the formula II. The reaction may be carried out at a temperature exceeding 100° C., preferably at the boiling point of the reaction mixture. The reaction having been completed, the solvent is removed—preferably in vacuo—and the residue is crystallized from a suitable solvent. Thus the corresponding hydrogen halide of the compound of the formula IV is obtained.

Alkanoic acids—such as acetic acid and propionic acid—may also be used as acidic condensing agents. This embodiment of our process may be preferably carried out by reacting 0.5 to 1.5 moles of a compound of the formula II with 0.5 to 1.5 moles of a compound of the formula III in the presence of an alkanoic acid under heating, advantageously at the boiling point of the alkanoic acid. Upon evaporation, the mixture and crystallization of the product, the compounds of the formula IV are obtained in the free base form.

By using the above embodiments of our process, the compounds of the formula IV and acid addition salts thereof are obtained in very pure form so that no special purification (e.g. chromatography) is required.

The compounds of the formula IV thus obtained may be subjected to reduction. If catalytic hydrogenation is carried out in the presence of Raney-nickel or a palladium or rhodium catalyst the tetrahydro-pyrido[1,2-a]pyrimidine derivatives of the formula V

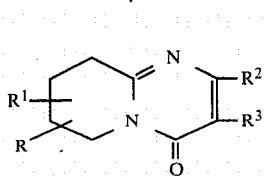

(wherein $R^1$, $R^2$, $R^3$ and R have the same meaning as stated above) while in the presence of a platinum or platinum oxide catalyst octahydro-pyrido[1,2-a]pyrimidine derivatives of the formula VI

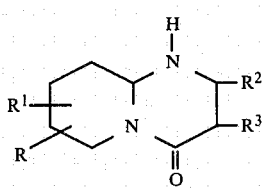

(wherein $R^1$, $R^2$, $R^3$ and R have the same meaning as stated above) are formed.

The tetrahydro-pyrido[1,2-a]pyrimidine derivatives of the formula V may also be converted into the octahydro derivatives of the formula VI by means of hydrogenation in the presence of a platinum or platinum oxide catalyst. This catalytic hydrogenation may be carried out at atmospheric pressure or under elevated pressure. As solvent, e.g. water, alkanols (e.g. methanol, ethanol etc.), organic acids (e.g. acetic acid etc.), ketones (e.g. acetone, methyl-ethyl-ketone etc.), esters (e.g. ethyl acetate etc.) or other solvents or mixtures thereof may be used.

A compound of the formula I may be transformed into another compound of the formula I by means of subsequent reactions which may be carried out by methods known per se. Thus, a carboxy derivative may be subjected to thermal decarboxylation to give the corresponding derivative in which there is a hydrogen atom at the place of the carboxylic group. A carboxylic acid may be esterified to give the corresponding ester or amidated to yield the optionally substituted acid amide. Thus, for example, 2,6-dimethyl-3-ethyl-9-carboxy-4-oxo-4H-pyrido[1,2-a]pyrimidine may be decarboxylated into the 2,6-dimethyl-3-ethyl-4-oxo-4H-pyrido[1,2-a]pyrimidine. The alkyl groups may also be formed by selective dehalogenation of the corresponding halogenoalkyl derivatives. Thus, for example, methyl-3-chloroethyl-4-oxo-4H-pyrido[1,2-a]pyrimidine may be transformed into 2,6-dimethyl-3-ethyl-4-oxo-4H-pyrido[1,2-a]pyrimidine by forming the corresponding Grignard compound and subjecting the same to hydrolysis. The compounds of the formula I may be converted into their salts formed with therapeutically acceptable inorganic or organic acids (e.g. hydrochloric, hydrobromic, hydroiodic, sulfuric, nitric, phosphoric, acetic, formic, malic, citric, mandelic acid etc.). Salt formation is carried out by known methods by reacting the compounds of the formula I with an approximately equimolar amount of the corresponding acid in an organic solvent.

The compounds of the formula I may also be converted into their quaternary salts by reacting with the usual quaternarizing agents, such as alkyl halides (e.g. methyl bromide, ethyl bromide, ethyl iodide), dialkylsulfates (e.g. dimethyl sulfate, diethyl sulfate etc.), sulfonates (e.g. benzene sulfonate, p-toluene sulfonic acid), trialkyl phosphates, oxonium fluoroborates etc. As the reaction medium the solvents generally used in quaternization reactions may be used, such as aromatic hydrocarbons (e.g. benzene, toluene etc.), halogenated hydrocarbons (e.g. chloroform, chlorobenzene etc.), ketones (e.g. acetone etc.), alkyl cyanides (e.g. acetonitrile), nitro alkanes (e.g. nitromethane), formamides (e.g dimethylformamide), dimethylsulfoxide, hexamethylene phosphoric triamide etc.) and mixtures thereof.

The quaternary salts may be subjected to reduction. This may be carried out by methods know per se. One may use catalytic hydrogenation or complex metal hydrides (e.g. sodium borohydride, sodium cyano borohydride, sodium-bis- (ethoxy-methoxy)-aluminumhydride etc.). A preferred embodiment of this process resides in the use of complex metal hydrides in a solvent which depends on the reducing agent (e.g. water, aliphatic alcohols, aromatic hydrocarbons etc.).

According to a further feature of the present invention there are provided pharmaceutical compositions comprising as active ingredient a compound of the formula I, wherein R is hydrogen, halogen, lower alkyl, nitro, hydroxy, amino, lower alkoxy, carboxy or a derivative of the carboxy group;

$R^1$ is hydrogen, halogen or lower alkyl;

$R^2$ is an alkyl group having 1 to 16 carbon atoms;

$R^3$ is an alkyl group having 1 to 16 carbon atoms, a $C_{7-12}$ aralkyl group optionally halogeno-substituted on the aromatic ring; or a cycloalkyl-alkyl group having 6 to 12 carbon atoms;

$R^4$ is a lone pair of electrons or a hydrogen atom or a lower alkyl group;

the dotted lines represent optional bonds or a salt or quaternary salt thereof in admixture with suitable inert pharmaceutical carriers and/or excipients. The compositions may be formulated in solid (e.g. tablets, capsules, dragees, pills, coated pills etc.), or liquid (e.g. solution, emulsion or suspension) form. The compositions contain conventional carriers such as talc, magnesium stearate, water, polyethylene glycol etc. The compositions may also contain unusual additives (e.g. emulsifying agents, disintegrating agents, buffers etc.). The compositions may be prepared by methods of the pharmaceutical industry known per se.

The compositions of the present invention may contain, in addition to the compounds of the formula I further therapeutically active substances e.g. other analgesics (such as morphine), benzomorphane derivatives (e.g. phenazocine, pentazocine), phenyl-piperidine derivatives (e.g. petidine, nisentyle).

The daily active ingredient dosage may vary between wide ranges and depends on the specific circumstances of the application in caption. As a guideline it may be stated that the daily oral dosage is approximately between 1 and 300 mg. and may be administered as such or in several portions, while the parenteral daily dosage amounts to about 0.1 to 100 mg.

The compounds of the formula I possess useful analgesic and morphine-potentiating properties and are valuable analgesics having a novel action mechanism. In Table I the morphine-potentiating effect of these compounds is demonstrated.

TABLE I

| Test compound | $LD_{50}$ mmole/kg | i.v. dose for potentiating the effect of 5 mg. of morphine, mmole/kg. |
|---|---|---|
| 2,3,6-trimethyl-4-oxo-4H-pyrido[1,2-a]pyrimidine . HCl | 0.780 | 0.066 |
| 2,6-dimethyl-3-ethyl-4-oxo-4H-pyrido[1,2-a]pyrimidine . HCl | 0.796 | 0.021 |
| 2-methyl-3-ethyl-4-oxo-4H-pyrido[1,2-a]pyrimidine . HCl | 1.070 | 0.012 |
| 3,6-dimethyl-2-ethyl-4-oxo-4H-pyrido[1,2-a]pyrimidine . HCl | 0.120 | 0.0019 |
| 2-methyl-3-n-propyl-4-oxo-4H-pyrido[1,2-a]pyrimidine . HCl | 0.502 | 0.0105 |
| 2,6-dimethyl-3-n-propyl-4-oxo-4H-pyrido[1,2-a]pyrimidine . HCl | 0.316 | 0.0025 |
| Probon$^R$ | 0.607 | 0.069 |

The following Table proves the outstanding analgesic properties of 2,6-dimethyl-3-ethyl-4-oxo-4H-pyrido[1,2-a]pyrimidine hydrochloride (referred to further as Compound A) over the chemically related 2-methyl-3-ethyl-4-oxo-4H-pyrido[1,2-a]pyrimidine.HCl (Compound B) and 2,6,8-trimethyl-3-ethyl-4-oxo-4H-pyrido[1,2-a]pyrimidine.HCl (Compound C). The analgesic effect was tested on the hot-plate and algolytic tests. The results are summarized in Table II.

TABLE II

| Test compound | Hot plate test $ED_{50}$ mg./kg. p.o. | Algolytic test $ED_{100}$ mg./kg. p.o. |
|---|---|---|
| A | 68 | 420 |
| B | 330 | cannot be achieved |
| C | 580 | cannot be achieved |

Table III contains further comparative data concerning Compounds A, B and C.

TABLE III

| Test | $LD_{50}$ (mg./kg.) i.v. | (mg./kg.) s.c. | p.o. | $ED_{50}$ (mg./kg.) hot-plate i.v. | s.c. | p.o. | $ED_{50}$ (mg./kg.) algolytic (+5mg./kg morphine) | Narcosis potent $ED_{500}$ (mg./kg.) |
|---|---|---|---|---|---|---|---|---|
| A | 190 | 520 | 690 | 74 | 68 | 58 | effective per se<br>98 s.c. 420 s.c.<br>8.6 s.c. 52 s.c. | 19 s.c.<br>25 p.o. |
| B | 280 | 620 | 1000 | 100 | 180 | 300 | 2.75 i.v. 18 s.c. | 40 i.v.<br>98 p.o. |
| C | 120 | 820 | 1500 | 49 | 120 | 580 | 210 s.c. | 100 i.v.<br>290 p.o. |

The above data show the outstanding effects of Compound A which surpass significantly the activity of the chemically related compounds. The instant compounds proved to be active in the algolytic test too.

The following Table IV contains test results in which the analgesic activity of the compounds of the present invention is compared to that of Probon.

TABLE IV

| Test compound | $LD_{50}$ rats mg./kg. p.o. | i.v. | s.c. | Hot plate test $ED_{50}$ mg./kg.(rats) p.o. | i.v. | s.c. |
|---|---|---|---|---|---|---|
| 2,6-dimethyl-3-ethyl-4-oxo-4-H-pyrido[1,2-a]pyrimidine . HCl | 690 | 190 | 520 | 68 | — | 74 |
| 2-methyl-3-ethyl-4-oxo-4H-pyrido[1,2-a]pyrimidine . HCl | 1000 | 280 | 620 | 300 | 100 | 180 |
| 2,6,8-trimethyl-3-ethyl-4-oxo-4H-pyrido[1,2-a]-pyrimidine . HCl | 1500 | 120 | 820 | 580 | 49 | 120 |
| 2,6-dimethyl-3-n-propyl-4-oxo-4H-pyrido[1,2-a]-pyrimidine . HCl | 1000 | — | 1200 | — | — | 48 |
| 2,9-dimethyl-3-ethyl-4-oxo-4H-pyrido[1,2-a]pyrimidine HCl | 820 | — | — | 310 | — | — |
| 2,7-dimethyl-3-ethyl-4-oxo-4H-pyrido[1,2-a]pyrimidine . HCl | 900 | 175 | 800 | 500 | 75 | 150 |
| 2-methyl-3-ethyl-7-chloro-4-oxo-4H-pyrido[1,2-a]-pyrimidine . HCl | 1100 | — | — | 98 | — | — |
| 2,3,6-trimethyl-4-oxo-4H-pyrido[1,2-a]pyrimidine . HCl | — | 175 | — | 87 | — | — |
| 2-methyl-3-n-butyl-4-oxo-4H-pyrido[1,2-a]pyrimidine . HCl | 1100 | — | — | 251 | — | — |
| 2,6-dimethyl-3-n-butyl-4-oxo-4H-pyrido[1,2-a]pyrimidine . HCl | 1100 | — | — | 340 | — | — |
| 1,6-dimethyl-3-ethoxy-carbonyl-4-oxo-4H-6,7,8,9-tetrahydro-pyrido[1,2-a]-pyrimidinium-methosulfate (Probon) | 1600 | 220 | — | 220 | 50 | — |

The test methods used are disclosed in the following publications:

Hot plate test: Woolfe and McDonald J. Pharm. 80, 300 (1944) modified by Porszasz and Herr: Kiserletes Orvostudomany 2, 292 (1950).

Algolytic test: J. Knoll et. al: Animal and Clinical Pharmacological Techniques in Drug Evaluation Eds. Siegler, P. E. and Meyer J. II. Year Book Medical Pub. Chicago (1967) pages 305–321.

Toxicity: Litchfield J. T. and Wilcoxon: J. Pharmacol. Sci 54 (1965) 888.

Also novel analgesic methods of treatment are contemplated as part of the invention. Compounds of the Formula I and Ia are analgesic agents which may be administered to an animal, especially a mammal, in pain, preferably either orally, intravenously, or subcutaneously in an effective amount along with a pharmaceutically acceptable inert carrier. A preferred group of compounds are those of formula I wherein R is hydrogen, halogen, lower alkyl, nitro, hydroxy, amino, lower alkoxy, carboxy, lower-alkoxycarbonyl; benzyloxycarbonyl, phenoxycarbonyl, carbamoyl, N-lower-alkylcarbamoyl, N,N-diloweralkyl-carbamoyl, carboazido, carbohydrazido, or cyano; $R^1$ is hydrogen, halogen or lower alkyl; $R^2$ $C_1$ to $C_6$ alkyl; $R^3$ is $C_1$ to $C_6$ alkyl or benzyl; and $R^4$ is a single electron pair, hydrogen or lower alkyl and the dotted lines represent saturated or unsaturated bonds. Even more preferred are compounds of Formula I where R is 9-hydroxy or is 6-,7- or 8-carboxy, loweralkoxycarbonyl, benzyloxycarbonyl, phenoxycarbonyl, carbamoyl, N-loweralkyl-carbamoyl, N,N-diloweralkyl-carbamoyl, carboazido, carbohydrazido or cyano.

Another analgesic method of treatment contemplated by the invention involves administering to an animal afflicted with pain an analgesically effective amount of morphine in combination with an effective amount of a compound of Formula I as defined in the preceding paragraph. Preferably the morphine and the compound of Formula I which potentiates the morphine are administered intravenously to the animal. Of course either of the methods of treatment described above may be carried out with a pharmaceutically acceptable acid addition or quaternary ammonium salt of a compound of Formula I.

Yet another period of treatment contemplated by the invention involves an antibacterial method of treatment. The compounds used in the antibacterial method of treatment are of the formula Ib

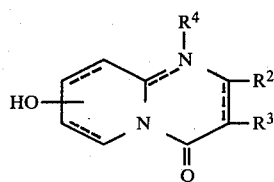

or pharmaceutically acceptable acid addition or quaternary ammonium salts thereof wherein $R^2$ is $C_1$ to $C_6$ alkyl;

$R^3$ is $C_1$ to $C_6$ alkyl or benzyl; and $R^4$ is a single electron pair, hydrogen or lower alkyl; and the dotted lines indicate saturated or unsaturated bonds. A preferred group of compounds are as defined above except that the hydroxy group is fixed in the 9-position of the pyrido(1,2-a)Pyrimidine skeleton. The preferred method of administration of these compounds to an afflicted animal, especially a mammal, is oral adminstration. However, any method of parenteral administration is also contemplated as well especially subcutaneous, intramuscular and topical adminstration.

Further details of the present invention are to be found in the Examples without limiting the scope of our invention to the Examples. The starting material used in our process are known compounds.

SPECIFIC EXAMPLES

Example 1

10.8 g. of 2-amino-6-methylpyridine are reacted with 14.4 g. of ethyl 2-methylacetacetate in a mixture of 46 g. of phosphorus oxychloride and 7.0 g. of polyphosphoric acid at 100° C. for 3 hours. The initially violent hydrogent chloride gas evolution gradually ceases. The reaction mixture is treated with 100 ml. of ethanol at a temperature of 70° to 80° C., whereupon the mixture is allowed to stand in a refrigerator overnight. The precipitated cystals are filtered off, washed with ethanol and dried. 20.2 g. (90%) of 2,3,6-trimethyl-4-oxo-4H-pyrido[1,2-a]pyrimidine hydrochloride are obtained, melting at 215° to 220° C. after recrystallization from a mixture of ethanol and ether.

Analysis for $C_{13}H_{16}N_2O.HCl$: Calculated: C=58.81%, H=5.83%, N=12.47%, Cl=15.78%; Found: C=58.48%, H=5.83%, N=12.28%, Cl=15.62%.

Following the procedure described above but using ethyl 2-n-propylacetacetate in place of ethyl 2-methylacetacetate, 2,6-dimethyl-3-n-propyl-4-oxo-4H-pyrido[1,2-a]pyrimidine hydrochloride is obtained, melting at 180° to 185° C.

Analysis for $C_{13}H_{16}N_2O.HCl$: Calculated: C=61.78%, N=6.78%, N=11.08%, Cl=14.03%; Found: C=61.52%, N=6.98%, N=11.03%, Cl=13.95%.

Following the procedure described above but using ethyl-2-n-butylacetacetate in place of ethyl-2-methylacetacetate, 2,6-dimethyl-3-n-butyl-4-oxo-4H-pyrido[1,2-a]pyrimidine hydrochloride is obtained, melting at 216° to 217° C.

Analysis for $C_{14}H_{18}N_2O.HCl$: Calculated: C=63.03%, H=7.17%, N=10.50%, Cl=13.28%; Found: C=62.65%, H=6.96%, N=10.68%, Cl=13.46%.

Following the procedure described above but using ethyl-2-n-decylacetacetate in place of ethyl-2-methylacetacetate, 2,6-dimethyl-3-n-decyl-4-oxo-4H-pyrido[1,2-a]pyrimidine hydrochloride is obtained, melting at 185° to 187° C.

Analysis for $C_{20}H_{30}N_2O.HCl$: Calculated: C=68.45%, H=8.90%, N=7.98%, Cl=10.10%; Found: C=68.35%, H=8.72%, N=7.92%, Cl=10.15.

Following the procedure described above but using ethyl-2-benzylacetacetate in place of ethyl-2-benzylacetacetate, 2,6-dimethyl-3-benzyl-4-oxo-4H-pyrido[1,2-a]pyrimidine hydrochloride is obtained, melting at 186° to 191° C.

Analysis for $C_{17}H_{16}N_2O.HCl$: Calculated: C=67.89%, H=5.70%, N=9.31%, Cl=11.79% Found: C=68.25%, H=6.13%, N=9.48%, Cl=11.06%.

Following the procedure described above but using ethyl 2-isobutylacetacetate in place of ethyl 2-methylacetacetate, 2,6-dimethyl-3-isobutyl-4-oxo-4H-pyrido[1,2-a]pyrimidine hydrochloride is obtained, melting at 178° to 185° C.

Analysis for $C_{14}H_{18}N_2O.HCl$: Calculated: C=63.03%, H=7.17%, N=10.50%, Cl=13.28%; Found: C=62.65%, H=6.86%, N=10.68%, Cl=13.46%.

Following the procedure described above but using ethyl-2-methyl-3-oxo-valerate in place of ethyl-2-methylacetacetate, 3,6-dimethyl-2-ethyl-4-oxo-4H-pyrido[1,2-a]pyrimidine hydrochloride, melting at 196° to 202° C. is obtained.

Analysis for $C_{12}H_{14}N_2O.NCl$: Calculated: C=60.38%, H=6.33%, N=11.73%, Cl=14.85%; Found: C=60.11%, H=6.70%, N=11.68%, Cl=14.56%.

Following the procedure described above but using ethyl-2-ethylacetacetate in place of ethyl-2-methylacetacetate and 2-aminopyridine instead of 2-amino-6-methylpyridine, 2-methyl-3-ethyl-4-oxo-4H-pyrido[1,2-a]pyrimidine hydrochloride, melting at 185° to 190° is obtained.

Analysis for $C_{11}H_{12}O.HCl$: Calculated: C=58.81%, H=5.83%, N=12.47%, Cl=15.78%; Found: C=58.41%, H=5.83%, N=12.62%, Cl=15.65%.

Following the procedure described above but using 2-aminopyridine and ethyl-2-n-propylacetacetate as starting compounds, 2-methyl-3-n-propyl-4-oxo-4H-pyrido[1,2-a]pyrimidine hydrochloride, melting at 210° to 215° is obtained.

Analysis for $C_{12}H_{14}N_2O.HCl$: Calculated: C=60.38%, H=6.33%, N=11.73%, Cl=14.85%; Found: C=60.45%, H=6.20%, N=11.82%, Cl=14.80%.

Following the procedure described above but using 2-aminopyridine and ethyl-2-n-butylacetacetate as starting compounds, 2-methyl-3-n-butyl-oxo-4H-pyrido[1,2-a]pyrimidine hydrochloride, melting at 220° to 222° C. is obtained.

Analysis for $C_{13}H_{16}N_2O.HCl$: Calculated: C=61.78%, H=6.78%, N=11.08%, Cl=14.03%; Found: C=61.89%, H=6.80%, N=11.00%, Cl=13.95%.

Following the procedure described above but using 2-aminopyridine and ethyl-2-n-decylacetacetate as starting compounds, 2-methyl-3-n-decyl-4-oxo-4H-pyrido-[1,2-a]pyrimidine hydrochloride is obtained, M.P.=200° to 202° C.

Analysis for $C_{19}H_{28}N_2O.HCl$: Calculated: C=67.74%, H=8.68%, N=8.31%, Cl=10.52%; Found: C=67.81%, H=8.75%, N=8.19%, Cl=10.40%.

Following the procedure described above but using 2-aminopyridine and ethyl-2-benzylacetacetate as starting compounds, 2-methyl-3-benzyl-4-oxo-4H-pyrido[1,2-a]pyrimidine hydrochloride is obtained, M.P. 180° to 190° C.

Analysis for $C_{16}H_{14}N_2O.HCl$: Calculated: C=67.02%, H=5.27%, N=9.77%, Cl=12.36%; Found: C=67.14%, H=5.25%, N=9.90%, Cl=11.98%.

Following the procedure described above but using 2-aminopyridine and ethyl-2-[(4-chlorophenyl)-methyl]-acetacetate as starting compounds, 2-methyl-3-[(4chlorophenyl)-methyl]-4-oxo-4H-pyrido[1,2-a]pyrimidine hydrochloride is obtained, M.P. 175° to 180° C.

Analysis for $C_{16}H_{13}N_2OCl.HCl$: Calculated: C=67.25, H=4.94%, N=9.80%, Cl=12.41%; Found: C=67.01%, H=5.03%, N=9.86%, Cl=12.25%.

Example 2

10.8 g. of 2-amino-6-methylpyridine are reacted with 15.8 g. of ethyl-2-ethylacetacetate in a mixture of 46. g. of phosphorus oxychloride and 7 g. of polyphosphoric acid at 120° to 130° C. for 3 hours. The intially violent hydrogen chloride gas evolution gradually ceases. The reaction mixture is treated with 100 ml. of ethanol at 70° to 80° C., whereupon the mixture is allowed to stand in a refrigerator overnight. The precipitated crystals are filtered off, washed with ethanol and dried. 22 g. (92%) of 2,6-dimethyl-3-ethyl-4-oxo-4H-pyrido[1,2-a]pyrimidine hydrochloride are obtained, M.P. 233° C. after recrystallization from a mixture of ethanol and ether.

Analysis for $C_{12}H_{14}N_2O.HCl$: Calculated: C=60.38%, H=6.33%, N=11.74%, Cl=14.85%; Found: C=60.44%, H=6.40%, N=11.90%, Cl=14.61.

Example 3

12.8 g. of 2-amino-5-chloropyridine are reacted with 15.8 g. of ethyl-2-ethylacetacetate in a mixture of 46 g. of phosphorus oxychloride and 7 g. of polyphosphoric acid at 120° to 130° C. for 3 hours. The initially violent hydrogen chloride gas evolution gradually ceases. The reaction mixture is treated with 100 ml. of water at 70° to 80° C. Upon cooling the pH-value of the mixture is adjusted to neutral with sodium carbonate. The aqueous reaction mixture is shaken with four 100-ml. portions of chloroform. The combined chloroform solutions, dried on sodium sulphate, are evaporated and ethyl acetate is distilled through the residue. 20.2 g. (91%) of 2-methyl-3-ethyl-7-chloro-4-oxo-4H-pyrido[1,2-a]pyrimidine are obtained, melting at 114° to 116° C. after recrystallization from a mixture of ethanol and ether.

Analysis for $C_{11}H_{11}N_2OCl$: Calculated: C=59.33%, H=4.98%, N=12.58%, Cl=15.92%; Found: C=59.20%, H=5.02%, N=12.39%, Cl=16.07%.

Following the procedures described above but using 2-amino-3-methylpyridine as an amine component, 2,9-dimethyl-3-ethyl-4-oxo-4H-pyrido[1,2-a]pyrimidine is obtained, melting at 90° to 92° C.

Analysis for $C_{12}H_{14}N_2O$: Calculated: C=71.26%, H=6.98%, N=13.85%; Found: C=71.20%, H=6.97%, N=13.70%.

Following the procedure described above but using 2-aminopyridine and ethyl-2-(cyclohexylmethyl)-acetacetate as starting compounds, 2-methyl-3-(cyclohexylmethyl)-4-oxo-4H-pyrido[1,2-a]pyrimidine is obtained, M.P. 112° to 114° C.

Analysis for $C_{16}H_{20}N_2O$: Calculated: C=74.97%, H=7.86%, N=10.93%; Found: C=75.10%, H=7.86%, N=10.95%.

Following the procedure described above but using 2-amino-6-methylpyridine and ethyl-2-(cyclohexylmethyl)-acetate as starting compounds 2,6-dimethyl-3-(cyclohexylmethyl)-4-oxo-4H-pyrido[1,2-a]pyrimidine is obtained, M.P. 124° to 126° C.

Analysis for $C_{17}H_{22}N_2O$: Calculated: C=75.52%, H=8.20%, N=10.36%; Found: C=75.40%, H=8.22%, N=10.29%.

Example 4

4.77 g. of 2,6-dimethyl-3-ethyl-4-oxo-4H-pyrido[1,2-a]pyrimidine hydrochloride are dissolved in 50 ml. of water and the pH-value of the mixture is adjusted to 7 with a 10% aqueous sodium carbonate solution. The reaction mixture is shaken with four 25-ml. portions of chloroform, the chloroform extracts are combined, dried over medium sulphate and evaporated. Ethyl acetate is distilled through the residue. 4.0 g. (99%) of 2,6-dimethyl-3-ethyl-4-oxo-4H-pyrido[1,2-a]pyrimidine are obtained, melting at 127° to 128° C. after recrystallization from a mixture of ethanol and ether.

Analysis for $C_{12}H_{14}N_2O$: Calculated: C=71.26%, H=6.98%, N=13.85%; Found: C=71.09%, H=6.98%, N=13.67%.

Following the procedure described above but starting from 2-methyl-3-n-decyl-4-oxo-4H-pyrido[1,2-a]pyrimidine hydrochloride, 2-methyl-3-n-decyl-4-oxo-4H-pyrido[1,2-a]pyrimidine is obtained, M.P. 66° to 67.5° C.

Analysis for $C_{19}H_{28}N_2O$: Calculated: C=75.96%, H=9.39%, N=9.32%; Found: C=76.11%, H=9.40%, N=9.34%.

Example 5

4.45 g. of 2-methyl-3-ethyl-7-chloro-4-oxo-4H-pyrido[1,2-a]-pyrimidine are dissolved in ethanol, with heating, then 25 ml. of a 28% by weight solution of hydrogen chloride in ethanol is added to the solution obtained. The precipitated crystals are filtered off and washed with ethanol. 5.01 g. (97%) of 2-methyl-3-ethyl-7-chloro-4-oxo-4H-pyrido[1,2-a]pyrimidine hydrochloride are obtained, M.P. 176° to 180° C.

Analysis for $C_{11}H_{11}N_2OCl.HCl$: Calculated: C=50.98%, H=4.57%, N=10.81%, Cl=13.68%; Found: C=50.82%, H=4.74%, N=10.92%, Cl=13.44%.

Example 6

4.04 g. of 2,6-dimethyl-3-ethyl-4-oxo-4H-pyrido(1,2-a)pyrimidine are dissolved in 50 ml. of ethanol and the solution is hydrogenated in the presence of 2 g. of Raney-nickel catalyst, previously washed to anhydrous with ethanol. Hydrogenation is performed under atmospheric pressure. In about seven hours the calculated amount of hydrogen is used up and the hydrogen consumption drops rapidly to zero. The catalyst is filtered off and the ethanol solution is evaporated. 4.10 g. (99.5%) of 2,6-dimethyl-3-ethyl-4-oxo-6,7,8,9-tetrahydro-4H-pyrido(1,2-a)pyrimidine are obtained as a pale-yellow non-crystallizing oil, which can be distilled under a pressure of 25 mmHg of 190° C.

Analysis for $C_{12}H_{18}N_2O$: Calculated: C=69.87%, H=8.80%, N=13.58%; Found: C=69.82%, H=8.96%, N=13.62%.

When, in the procedure described above, a 10% palladium on carbon catalyst is used instead of Raney-nickel, a calculated amount of hydrogen is consumed in 10 hours and 2,6-dimethyl-3-ethyl-4-oxo-6,7,8,9-tetrahydro-4H-pyrido(1,2-a)pyrimidine is obtained as a non-crystallizing oil.

Example 7

A mixture of 10.8 g. of 2-amino-6-methyl-pyridine, 15.8 g. of ethyl-2-ethylacetate and 100 g. of polyphosphoric acid is stirred at 100° C. for 1.5 hours. The reaction mixture is diluted with 75 to 100 ml. of water, then its pH-value is adjusted to 7 with a 10% aqueous sodium hydroxide solution. The precipitated crystals are filtered off, washed with water and dried. 17.2 g. (85%) of 2,6-dimethyl-3-ethyl-4-oxo-4H-pyrido(1,2-a)pyrimidine are obtained, melting at 127° to 128° C. after recrystallization from a mixture of ethanol and ether. When the product is admixed with the product of Example 6, no melting point decrease is observed.

Example 8

Following the procedure described in Example 7 but using 0.02 moles of ethyl-2-ethylacetacetate, 2-methyl-3-ethyl-9hydroxy-4-oxo-4H-pyrido(1,2-a)pyrimidine is obtained, melting at 128° C. after recrystallization from a 70% aqueous ethanol solution. Yield: 73%.

Analysis for $C_{11}H_{12}N_2O_2$: Calculated: C=64.69%, H=5.92%; Found: C=64.90%, H=6.15%.

Example 9

Following the procedure described in Example 1, but reacting 0.02 moles of 2-amino-3-hydroxypyridine and 0.02 moles of ethyl-2-ethylacetacetate, 2-methyl-3-ethyl-9-hydroxy-4-oxo-4H-pyrido(1,2-a)pyrimidine hydrochloride is obtained, melting at 175° to 178° C. after recrystallization from a mixture of ethanol and ether. Yield: 59%.

Analysis for $C_{11}H_{12}N_2O_2.HCl$: Calculated: C=55.12%, H=5.47%, Cl$^-$=14.79%; Found: C=55.22%, H=5.51%, Cl$^-$=14.67%.

Example 10

Following the procedure described in Example 7 but reacting 0.02 moles of 2-amino-3-hydroxypyridine and 0.02 moles of ethyl-2-benzylacetacetate, 2-methyl-3-benzyl-9-hydroxy-4-oxo-4H-pyrido(1,2-a)pyrimidine is obtained, melting at 124° to 125° C., after recrystallization from ethanol. Yield: 70%.

Analysis for $C_{16}H_{14}N_2O_2$: Calculated: C=72.16%, H=5.30%; Found: C=71.97%, H=5.41%.

Example 11

Following the procedure described in Example 7 but reacting 0.02 moles of 2-amino-5-nitropyridine and 0.02 moles of ethyl-2-ethylacetacetate, 2-methyl-3-ethyl-7-nitro-4-oxo-4H-pyrido(1,2-a)pyrimidine is obtained. Yield: 38%. The product is contaminated with a small amount of starting 2-amino-5-nitropyridine, which can easily be eliminated by crystallization from ethanol. Melting point after two subsequent crystallizations from ethanol: 163° to 164° C.

Analysis for $C_{11}H_{11}N_3O_3$: Calculated: C=56.65%, H=4.75%; Found: C=56.50% H=4.60%.

Example 12

Following the procedure described in Example 3, but reacting 0.02 moles of 2-amino-5-nitropyridine and 0.02 moles of ethyl-2-ethylacetacetate, 2-methyl-3-ethyl-7-nitro-4-oxo-4H-pyrido(1,2-a)pyrimidine is obtained, melting at 164° to 165° C. after two subsequent recrystallizations from ethanol. Yield: 51%. The product does not show any melting point depression when admixed with the product of Example 11.

Example 13

0.02 moles of 2-amino-4-methylpyridine hydrochloride and 0.03 moles of ethyl-2-ethylacetacetate in 50 ml. of pyridine are refluxed for 16 hours. The solvent and the excess amount of ketoester are distilled off under reduced pressure and the residue is crystallized from a mixture of ethanol and ether. 2,8-dimethyl-3-ethyl-4-oxo-4H-pyrido (1,2-a)pyrimidine hydrochloride is obtained, melting at 192° to 198° C. Yield: 39%. After recrystallization from ethanol the product melts at 195° to 199° C.

Analysis for $C_{12}H_{14}N_2O \cdot HCl$: Calculated: C=60.38%, H=6.33%, Cl⁻=14.85%; Found: C=60.41%, H=6.38%, Cl⁻=14.67%.

Example 14

0.02 moles of 2-aminopyridine hydrobromide and 0.03 moles of ethyl-2-n-propylacetacetate are reacted as described in Example 13 to afford 2-methyl-3-n-propyl-4-oxo-4H-pyrido(1,2-a)pyrimidine hydrobromide. Yield: 49%. The product sublimates at 210° C. after recrystallization from ethanol.

Analysis for $C_{12}H_{14}N_2O \cdot HBr$: Calculated: C=50.90%, H=5.34%; Found: C=50.81%, H=5.20%.

The free base deliberated from the hydrogen bromide salt in a conventional manner, melts at 57° to 58° C. The 2-methyl-3-n-propyl-4-oxo-4H-pyrido(1,2-a)pyrimidine obtained is crystallized from n-hexane. The product does not give any melting point depression when admixed with the base set free from 2-methyl-3-n-propyl-4-oxo-4H-pyrido(1,2-a)pyrimidine hydrochloride.

Analysis for $C_{12}H_{14}N_2O$: Calculated: C=71.26%, H=6.98%; Found: C=71.32%, H=6.86%.

Example 15

Following the procedure described in Example 13 but reacting 0.02 moles of 2-aminopyridine hydroiodide and 0.03 moles of ethyl-2-n-propylacetacetate 2-methyl-3-n-propyl-4-oxo-4H-pyrido-(1,2-a) pyrimidine hydroiodide is obtained, melting at 200° to 210° C. after recrystallization from ethanol. Yield 53%.

Analysis for $C_{12}H_{14}N_2O \cdot HI$: Calculated: C=43.66%, H=4.58%; Found: C=43.41%, H=4.67%.

The free base liberated from the hydrogen iodide salt in a conventional manner, melts at 58° to 59° C. The product does not give any melting point depression when admixed with 2-methyl-3-n-propyl-4-oxo-4H-pyrido(1,2-a)pyrimidine obtained in Example 14.

Example 16

0.02 moles of 2-aminonicotinic acid and 0.02 moles of ethyl-2-ethylacetacetate in 20 g. of polyphosphoric acid are stirred at 145° C. for one hour. The reaction mixture is diluted with 10 ml. of water and its pH-value is adjusted to neutral with a 10% aqueous sodium hydroxide solution. The precipitated oily product is extracted with three 25 ml. portions of chloroform, the chloroform extracts are combined, dried and evaporated. 2-methyl-3-ethyl-9-carboxyl-4-oxo-4H-pyrido(1,2-a)pyrimidine is obtained, melting at 177° to 179° after recrystallization from ethanol. Yield: 41%.

Analysis for $C_{12}H_{12}N_2O_3$: Calculated: C=62.02%, H=5.21%; Found: C=62.10%, H=5.13%.

Example 17

Following the procedure described in Example 7 but reacting 0.02 moles of 2-amino-4-ethoxycarbonylpyridine and 0.02 moles of ethyl-2-ethylacetacetate 2-methyl-3-ethyl-8-ethoxycarbonyl-4-oxo-4H-pyrido(1,2-a)pyrimidine is obtained, melting at 94° to 96° C. after crystallization of ethanol. Yield 64%.

Analysis for $C_{14}H_{16}N_2O_3$: Calculated: C=64.60%, H=6.20%; Found: C=64.44%, H=6.24%.

Example 18

0.02 moles of 2-amino-4-ethoxycarbonylpyridine and 0.02 moles of ethyl-2-ethylacetacetate are stirred in a mixture of 10 ml. of phosphorous oxychloride and 2 g. of polyphosphoric acid at 120° C. for 2 hours. The reaction mixture is treated with 20 ml. of ethanol at 70° to 80° C., whereupon it is neutralized with a 10% (w/v) aqueous sodium hydroxide solution with ice cooling. The ethanol is evaporated, the residue is extracted with four 25-ml. portions of chloroform and the combined extracts are dried and evaporated. The evaporation residue is triturated with ether to give crystalline 2-methyl-3-ethyl-8-ethoxycarbonyl-4-oxo-4H-pyrido-(1,2-a)pyrimidine, melting at 95° to 96° C. Yield 42%. The product does not give any melting point depression when admixed with the product of Example 17.

Example 19

0.01 moles of 2,6-dimethyl-3-ethyl-4-oxo-4H-pyrido(1,2-a)pyrimidine are dissolved in 20 ml. of acetone, 0.03 moles of methyl-iodide are added and the mixture is kept in a bomb tube at 150° C. for 24 hours. The solution is then concentrated to 10 ml. and allowed to stand for 24 hours. 1,2,6-trimethyl-3-ethyl-4-oxo-4H-pyrido(1,2-a)pyrimidine iodide precipitates, melting at 203° to 206° C. after recrystallization from ethanol. Yield: 86%.

Analysis for $C_{13}H_{17}IN_2O$: Calculated: C=45.37%, H=4.98%; Found: C=45.16%, H=4.81%.

Example 20

Following the procedure described in Example 6, starting from 0.02 moles of 2-methyl-3-ethyl-4-oxo-4H-pyrido-(1,2-a)pyrimidine colorless, viscous 2-methyl-3-ethyl-6,7,8,9-tetrahydro-4-oxo-4H-pyrido(1,2-a)pyrimidine is obtained, which can be distilled at 146° to 148° C./6 mmHg. Yield (using Raney-nickel as a catalyst): 96%.

(using palladium on charcoal as a catalyst): 97%. After a short standing the product crystallizes.

Analysis for $C_{11}H_{16}N_2O$: Calculated: C=68.72%, H=8.39%; Found: C=68.67%, H=8.40%.

Example 21

0.01 moles of 2,6-dimethyl-3-ethyl-4-oxo-4H-pyrido(1,2-a)pyrimidine are dissolved in 20 ml. of acetone, 0.03 moles of methyl iodide are added and the mixture is kept in a bomb tube at 150° C. for 24 hours. The solution is evaporated to dryness, the residue is dissolved in 15 ml. of methanol and a solution of 0.05 moles of sodium tetrahydroborate(III) in 10 ml. of water is added. After 4 hours the methanol is distilled off and the aqueous phase is extracted with three 20-ml. portions of chloroform. The organic phase is dried, evaporated and added to the oily substance obtained are 10 ml. of ethanol saturated with hydrochloric acid. 1,2,6-trimethyl-3-ethyl-1,2,3,6,7,8,9,9a-octahydro-4-oxo-4H-pyrido(1,2-a)pyrimidine hydrochloride is obtained, while crystallizes when triturated with ether. The product obtained after recrystallization from a mixture of acetone and ether sublimates over 206° C. Yield: 41%.

Analysis for $C_{13}H_{20}N_2O \cdot HCl$: Calculated: C=60.81%, H=8.24%, Cl⁻=13.81%; Found: C=60.64%, H=8.12%, Cl⁻=13.96%.

Example 22

10 g. of 3-ethyl-2,6-dimethyl-4-oxo-4H-pyrido(1,2-a)pyrimidine are dissolved in 100 ml. of ethanol and 12 g. of fumaric acid in 100 ml. of ethanol are added. The mixture is brought to a boil and then cooled. The precipitated crystals are filtered off, washed with a small portion of ethanol and dried. 12.5 g. (78.5%) of di-(3-ethyl-2,6-dimethyl-4-oxo-4H-pyrido[1,2-a]pyrimidinium)-fumarate are obtained, melting at 185° to 186° C. after recrystallization from ethanol.

Analysis for $C_{28}H_{32}N_4O_6$: Calculated: C=64.60%, H=6.20%, N=10.76%; Found: C=64.35%, H=6.24%, N=10.40%.

Example 23

10 g. of 3-ethyl-2,6-dimethyl-4-oxo-4H-pyrido(1,2-a)pyrimidine are dissolved in 100 ml. of ethylmethyl ketone with heating and to the solution obtained a solution of 12 g. of maleic acid in 100 ml. of ethylmethyl ketone is added. The reaction mixture is brought to a boil, the cooled. The precipitated crystals are filtered off and washed with a small portion of ethylmethyl ketone. 14.0 g. (87.9%) of hydrogen- (3-ethyl-2,6-dimethyl-4-oxo-4H-pyrido[1,2-a]pyrimidinium)maleate are obtained, melting at 137° to 138° C. after recrystallization from ethanol.

Analysis for $C_{16}H_{18}N_2O_5$: Calculated: C=60.36%, H=5.70%, N=8.80%; Found: C=60.35%, H=5.72%, N=8.65%.

Example 24

10 g. of 3-ethyl-2,6-dimethyl-4-oxo-4H-pyrido(1,2-a)pyrimidine are dissolved in 100 ml. of acetone with heating and a solution of 7 g. of salicylic acid in 100 ml. of acetone is added. The reaction mixture is brought to a boil, then cooled. The precipitated crystals are filtered off, washed with acetone and dried. 11.5 g. (67.6%) of 3-ethyl-2,6-dimethyl-4-oxo-4H-pyrido(1,2-a)pyrimidinium salicylate are obtained, melting at 126° to 128° C. after recrystallization from ethanol.

Analysis for $C_{19}H_{20}N_2O_4$: Calculated: C=67.04%, H=5.92%, N=8.22%; Found: C=67.50%, H=5.94%, N=8.25%.

Example 25

10 g. of 3-ethyl-2,6-dimethyl-4-oxo-4H-pyrido(1,2-a)pyrimidine are dissolved in 30 ml. of ethanol with heating and to the solution obtained a solution of 19.2 g. of citric acid in 100 ml. of ethanol is added. The reaction mixture is brought to a boil, then cooled. The precipitated crystals are filtered off, washed with ethanol and dried. 18.2 g. (92.4%) of hydrogen-(3-ethyl-2,6-dimethyl-4-oxo-4H-pyrido[1,2-a]pyrimidinium)-citrate are obtained, melting at 136° to 137° C. after recrystallization from ethanol.

Analysis for $C_{18}H_{22}N_2O_8$: Calculated: C=54.83%, H=5.62%, N=7.10%; Found: C=55.08%, H=5.70%, N=7.01%.

Example 26

10 g. of 3-ethyl-2,6-dimethyl-4-oxo-4H-pyrido(1,2-a)pyrimidine are dissolved in 100 ml. of acetone with heating and to the solution obtained a solution of 13.4 g. of D,L-malic acid in 100 ml. of acetone is added. The reaction mixture is brought to a boil and then cooled. The precipitated crystals are filtered off, washed with acetone and dried. 11.5 g. (69.4%) of hydrogen-(3-ethyl-2,6-dimethyl-4-oxo-4H-pyrido[1,2-a]pyrimidinium)-2-hydroxysuccinate are obtained, melting at 141° to 142° C. after recrystallization from ethanol.

Analysis for $C_{28}H_{34}N_4O_7$: Calculated: C=62.44%, H=6.36%, N=10.40%; Found: CΔ62.47%, H=6.76%, N=10.43%.

Example 27

10.0 g. of 3-ethyl-2,6-dimethyl-4-oxo-4H-pyrido(1,2-a)pyrimidine are dissolved in 50 ml. of ethanol with heating and to the solution obtained 2.8 ml. of a 96 to 97% by weight aqueous sulphuric acid are added. The mixture is brought to a boil, then cooled. The precipitated crystals are filtered off, washed with ethanol and dried. 5 g. (33%) of hydrogen-(3-ethyl-2,6-dimethyl-4-oxo-4H-pyrido[1,2-a]pyrimidinium)-sulphate are obtained, melting at 199° to 200° C. after recrystallization from ethanol.

Analysis for $C_{12}H_{16}N_2O_5S$: Calculated: C=47.99%, H=5.40%, N=9.33%; Found: C=48.31%, H=5.51%, N=9.55%.

Example 28

Following the procedure described in Example 2 but using 2-amino-4-methylpyridine as a starting aminopyridine compound, 3-ethyl-2,8-dimethyl-4-oxo-4H-pyrido(1,2-a)pyrimidinium hydrochloride is obtained, melting at 195° to 200° C. after recrystallization from ethanol. Yield: 64%.

Analysis for $C_{12}H_{14}N_2O \cdot HCl$: Calculated: C=60.38%, H=6.33%, N=11.74%, Cl=14.85%; Found: C=60.42%, H=6.38%, N=11.82%, Cl=14.67%.

Example 29

Following the procedure described in Example 2 but using 2-amino-4,6-dimethylpyridine as a starting aminopyridine, 3-ethyl-2,6,8-trimethyl-4-oxo-4H-pyrido(1,2-a)pyrimidinium hydrochloride, melting at 198° to 205° C. after recrystallization from ethanol.

Analysis for $C_{13}H_{16}N_2O \cdot HCl$: Calculated: C=61.78%, H=6.78%, N=11.08%, Cl=14.03%; Found: C=62.08%, H=6.81%, N=11.17%, Cl=13.82%.

Example 30

Following the procedure described in Example 2 but using 2-ethyl-3-oxocapric acid ethylester as an oxo-ester, 3-ethyl-6-methyl-3-n-propyl-4-oxo-4H-pyrido(1,2-a)pyrimidinium hydrochloride is obtained, melting at 160° to 165° C. after recrystallization from ethanol. Yield 75%.

Analysis for $C_{14}H_{18}N_2O \cdot HCl$: Calculated: C=63.03%, H=7.18%, N=10.50%, Cl=13.29%; Found: C=63.28%, H=7.32%, N=10.58%, Cl=13.15%.

Example 31

A mixture of 2.16 g. of 2-amino-5-methylpyridine and 3.16 g. of ethyl-2-ethylacetacetate in a mixture of 4.6 ml. of phosphorus oxychloride and 1.4 g. of polyphosphoric acid is stirred at 120° to 130° C. for 45 minutes. The initially violent gas evolution gradually ceases. The reaction mixture is treated with 20 ml. of ethanol and is crystallized upon cooling and scratching. The precipitated crystals are filtered off. The 4.6 g. of hydrochloric acid salt are dissolved in 20 ml. of water and the solution is neutralized with 20% (w/v) aqueous sodium carbonate solution. The precipitated crystals are filtered off, washed with water and dried. 2 g. (49%) of 3-ethyl-2,7-dimethyl-4-oxo-4H-pyrido(1,2-a)pyrimidine are obtained, melting at 154° to 156° C. after recrystallization from methanol.

Analysis for $C_{12}H_{14}N_2O$: Calculated: $C=71.42\%$, $H=6.98\%$, $N=13.85\%$; Found: $C=71.42\%$, $H=7.08\%$, $N=13.91\%$.

We claim:

1. A compound of the formula

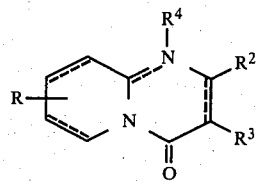

or a pharmaceutically acceptable acid addition or quaternary ammonium salt thereof wherein R is carboxy in the 6-, 7- or 8-position or lower alkoxycarbonyl in the 6-, 7- or 8-position;

$R^2$ is $C_1$ to $C_6$ alkyl;

$R^3$ is $C_1$ to $C_6$ alkyl; and $R^4$ is a single election pair, hydrogen or lower alkyl; and the dotted lines represent saturated or unsaturated bonds.

2. 2-methyl-3-ethyl-8-ethoxycarbonyl-4-oxo-4H-pyrido(1,2-a)pyrimidine or a pharmaceutically acceptable acid addition or quaternary ammonium salt thereof.

3. An analgesic method of treatment which comprises the step of administering to an afflicted animal an analgesically effective amount of a compound of the formula

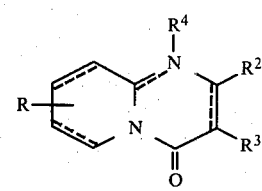

or a pharmaceutically acceptable acid addition or quaternary ammonium salt thereof, wherein R is carboxy in the 6-, 7- or 8-position or lower alkoxycarbonyl in the 6-, 7- or 8-position;

$R^2$ is $C_1$ to $C_6$ alkyl;

$R^3$ is $C_1$ to $C_6$ alkyl; and $R^4$ is a single electron pair, hydrogen or lower alkyl; and the dotted lines represent saturated or unsaturated bonds.

4. The analgesic method of treatment defined in claim 3 wherein the compound administered is 2-methyl-3-ethyl-8-ethoxycarbonyl-4-oxo-4H-pyrido(1,2,-a)pyrimidine or a pharmaceutically acceptable acid addition or quaternary ammonium salt thereof.

* * * * *